United States Patent [19]

Schieb et al.

[11] Patent Number: 5,345,012

[45] Date of Patent: Sep. 6, 1994

[54] PROCESS FOR THE PREPARATION OF DINITROTOLUENE

[75] Inventors: Thomas Schieb, Rösrath; Gerhard Wiechers; Rudolf Sundermann, both of Leverkusen; Uwe Zarnack, Brunsbüttel, all of Fed. Rep. of Germany

[73] Assignee: Bayer Aktiengesellschaft, Leverkusen, Fed. Rep. of Germany

[21] Appl. No.: 147,654

[22] Filed: Nov. 3, 1993

[30] Foreign Application Priority Data

Nov. 13, 1992 [DE] Fed. Rep. of Germany ........ 4309140
Mar. 22, 1993 [DE] Fed. Rep. of Germany ........ 4309140

[51] Int. Cl.$^5$ ............................................. C07C 205/06
[52] U.S. Cl. ................................................... 568/934
[58] Field of Search ........................................ 568/934

[56] References Cited

U.S. PATENT DOCUMENTS

| | | | |
|---|---|---|---|
| 2,012,985 | 9/1935 | Cartner | 568/934 |
| 2,947,791 | 8/1960 | Adams | 568/934 |
| 3,053,908 | 9/1962 | Kouba et al. | 568/934 |
| 3,157,706 | 11/1964 | Ozeki et al. | 568/934 |
| 3,178,481 | 4/1965 | Hauze | 568/934 |
| 3,204,000 | 8/1965 | Samuelson | 568/934 |
| 3,928,475 | 12/1975 | Dassel | 260/645 |
| 4,021,498 | 5/1977 | Alexanderson et al. | 260/645 |
| 4,091,042 | 5/1978 | Alexanderson et al. | 260/645 |
| 4,453,027 | 6/1984 | Vaidyanathan | 568/937 |
| 4,663,490 | 5/1987 | Gerken et al. | 568/934 |
| 4,935,557 | 6/1990 | Carr et al. | 568/934 |

FOREIGN PATENT DOCUMENTS 436443 7/1991 European Pat. Off. .
1372978 10/1963 France .

OTHER PUBLICATIONS

Muspratt and Hofmann, Liebig Ann. Chem. 57, 201 (1846).
Ullman, Encyclopädie de technischen Chemie, fourth edition, vol. 17, p. 392 (1972).

*Primary Examiner*—Joseph E. Evans
*Attorney, Agent, or Firm*—Joseph C. Gil; Lyndanne M. Whalen

[57] ABSTRACT

A continuous process for the preparation of isomeric mixtures of dinitrotoluene by a single stage nitration of toluene under adiabatic conditions. The reaction enthalpy is used for the removal by distillation of the water of reaction formed during nitration. In this process, toluene is reacted with a nitrating acid having from about 80 to about 100% by weight of an inorganic component having a specified composition and from about 0 to about 20% by weight of an organic component having a specified composition.

5 Claims, No Drawings

PROCESS FOR THE PREPARATION OF DINITROTOLUENE

BACKGROUND OF THE INVENTION

The present invention relates to a process for the preparation of dinitro-toluene by a single stage nitration of toluene with nitrating acid under adiabatic conditions.

It is known that aromatic compounds can be converted into the corresponding nitroaromatic compounds by nitration with mixtures of sulfuric acid and nitric acid, also known as nitrating acid (See, e.g., Muspratt and Hofmann, *Liebigs Ann. Chem.* 57, 201 (1846).

On a large scale, nitration reactions have been and often still are carried out isothermally (i.e., the heat of reaction is removed at the site of its production (stirrer vessel, loop reactor, etc.) by a cooling agent). This also applies to the large scale production of dinitrotoluene. Dinitrotoluene is generally produced in two stages under isothermal conditions (See, e.g., Ullman, *Encyclopadie der technischen Chemie*, fourth edition, Volume 17, p.392).

The main disadvantage of this known procedure is that a large amount of energy is required both for maintaining the isothermal reaction conditions (cooling) and for the subsequent removal of the water of reaction from the acid phase by distillation (heating up).

SUMMARY OF THE INVENTION

It is an object of the present invention to provide a new process for the dinitration of toluene in which the heat of the reaction (enthalpy) is used to remove the water of reaction from the acid phase produced during the nitration process.

It is also an object of the present invention to provide an energy efficient, continuous process for the production of dinitrotoluene under adiabatic conditions.

These and other objects which will be apparent to those skilled in the art are accomplished by reacting toluene with a nitrating acid having a specified composition under adiabatic conditions, continuously removing some of the reactive mixture at a temperature of at least 120° C., separating the recovered reaction mixture into an upper product phase and a lower acid phase, working up the product phase to recover dinitrotoluene, removing water from the lower acid phase by flash evaporation, adding from 50 to 100% by weight nitric acid to the lower acid phase, and recycling the acid phase.

DETAILED DESCRIPTION OF THE INVENTION

The nitration of aromatic compounds under adiabatic reaction conditions has been disclosed in numerous prior Patent Specifications. See, e.g., U.S. Pat. Nos. 3,928,475; 4,021,498; 4,091,042; and 4,453,027; and EP-A-O 436 443. Each of these prior art processes, however, is used only for mononitration. Toluene is not mentioned in any of the examples given in these disclosures as the aromatic compound to be nitrated. This is probably due to the fact that dinitration requires considerably more drastic reaction conditions (the use of at least equivalent quantities of nitrating acid and higher reaction temperatures) than mononitration. The formation of large quantities of unwanted by-products would be expected, regardless of the nature of the aromatic compound to be nitrated. The readily oxidizable methyl group of toluene would not be expected to survive the drastic conditions of dinitration.

It has now been found that dinitration of aromatic compounds, including the dinitration of toluene, can be carried out satisfactorily under the adiabatic reaction conditions described below.

The present invention is directed to a process for the continuous preparation of isomeric mixtures of dinitrotoluene by the nitration of toluene. In this process, toluene is reacted with nitrating acid in a single stage under adiabatic conditions in a continuously operating reactor. The nitrating acid is made up of (i) from about 80 to about 100% by weight of an inorganic component and (ii) from 0 to about 20% by weight of an organic component. The inorganic component is substantially composed of from about 60 to about 90% by weight of sulfuric acid, from about 1 to about 20% by weight of nitric acid and at least 5% by weight of water. The organic component is composed of from about 70 to about 100% by weight of dinitrotoluene isomers and from about 0 to about 30% by weight of by-products. The molar ratio of nitric acid to toluene is maintained at a level of at least 2:1. The reaction mixture leaves the reactor continuously at a temperature of at least 120° C. and is then separated into an upper product phase and a lower acid phase. The product phase is worked up in known manner to recover the product dinitrotoluene. At least 10% by weight of the water is removed from the acid phase by distillation (flash evaporation), optionally with concomitant supply of heat. The acid phase is then returned to the beginning of the process after the addition of from about 50 to about 100% by weight nitric acid.

The nitrating acid used in the process of the present invention is made up of (i) from about 80 to about 100% by weight of an inorganic component composed substantially of from about 60 to about 90% by weight, preferably from about 65 to about 85% by weight, of sulfuric acid, from about 1 to about 20% by weight, preferably from about 1 to about 15% by weight, of nitric acid, and at least 5% by weight, preferably not less than 10% by weight, of water; and (ii) from about 0 to about 20% by weight of an organic component composed of from about 70 to about 100% by weight of dinitrotoluene isomers and from about 0 to about 30% by weight of organic by-products. When nitrating acids having a nitric acid content of from about 5 to about 20% by weight are used, the inlet temperature is preferably below 100° C. When nitrating acids having a nitric acid content of from 1 to 15% are used, the inlet temperature is preferably above 100° C.

The organic by-products which may be present in the organic component of the nitrating acid include: mononitrotoluenes, trinitrotoluene, cresols and carboxylic acids. These by-products do not interfere with the course of the continuous reaction cycle because they are oxidized to dinitrotoluene in a later cycle (mononitrotoluene), discharged when the product is washed under alkaline conditions (acids, cresols), oxidized to carbon dioxide and water or left in the product in trace amounts(trinitrotoluene).

At the beginning of the process, the nitrating acid is generally made up entirely of the inorganic component. However, because the process is a continuous process in which the inorganic acid phase containing organic components of the above-mentioned type is returned to the beginning of the process after the addition of nitric acid, the nitrating acid which is mixed with the toluene to be nitrated contains organic components of the above-mentioned type. While the process is in circulation, the nitrating acid produced from circulating acid and fresh nitric acid is preferably made up of from about 80 to about 99.9% by weight of inorganic component (i) and from about 0.1 to about 20% by weight of organic component (ii).

In the process of the present invention, the nitrating acid is continuously mixed with the toluene to be nitrated. The proportion of these components corresponds to a molar ratio of nitric acid to toluene of at least 2:1, preferably from 2:1 to 2.2:1.

Before mixing the nitrating acid and toluene, the temperature of the starting materials is preferably raised to a temperature selected on the basis of the nitric acid content of the nitrating acid. The temperature of the reactants may be raised to a temperature below 100° C., more preferably below 80° C. when the nitrating acid contains from about 5 to about 20% by weight of nitric acid. The temperature of the reactants may be raised above 100° C., preferably above 120° C., when the nitrating acid contains from about 1 to about 15% by weight of nitric acid.

Any reactor in which back mixing can be substantially prevented in a continuous operation is suitable in principle for carrying out the process of the present invention. Tubular reactors, for example, are suitable for this purpose. Tubular reactors made of high grade steel, tantalum, enamelled steel or glass are particularly preferred.

Any of the known mixing apparatus such as stirrers, rotor-stator systems, mixing pumps, nozzles and static mixers may be used to mix the starting materials.

There is generally no removal of heat during the nitration of the present invention (adiabatic conditions). The reaction mixture leaving the reactor after a sufficient residence time for complete reaction of the toluene put into the process, is generally at a temperature of at least 120° C., preferably from about 140° to about 220° C. The outlet temperature of the product mixture is at least 10° C. above the inlet temperature of the starting materials. External cooling may, in some cases, be used to prevent the temperature from rising too high.

After the hot reaction mixture has left the reactor it is subjected to phase separation. The mixture is separated into a product phase (upper phase) and an acid phase (lower phase).

After the product phase has been worked up by any of the known procedures (e.g., washing out the traces of acid adhering to the product), the product recovered is substantially (i.e., generally at least 98% by weight) isomeric dinitrotoluene containing less than 7% by weight, preferably less than 6% by weight, of ortho-isomers. The product has a ratio by weight of 2,4-dinitrotoluene to 2,6-dinitrotoluene of 80±2:20±2. The amount of mononitrotoluene in the product is less than 2,000 ppm (by weight). Trinitrotoluene is present in less than 2,000 ppm (by weight).

In a preferred embodiment of the present invention, the product is crystallized rather than worked up by other known methods (e.g., washing out traces of adhering acid).

The hot acid phase obtained from phase separation is freed from at least 10% of the water by evaporation under vacuum, optionally with concomitant supply of heat. The remaining acid phase is then mixed with from about 50 to about 100% by weight, preferably from about 60 to about 70% by weight nitric acid, so that a nitrating acid having the composition indicated above is again obtained and returned to the beginning of the process.

The invention is explained in more detail in the following examples. All percentages given in these Examples are percentages by weight.

EXAMPLES

EXAMPLE 1

113.4 g/h (1.233 mol/h) of toluene and 1445.9 g/h of nitrating acid having the composition 73.6:11.6:14:8 (parts by weight of $H_2SO_4:HNO_3:H_2O$), corresponding to a molar ratio of nitric acid to toluene of 2.16:1, were continuously pumped from two separate dosing pumps at 40° C. (temperature of the starting materials) into a reactor which was designed so that back mixing would not occur. The reactor used for this purpose was a 20 m long reaction tube of high grade steel having an internal diameter of 0.6 mm. The components were mixed immediately before their entry into the reactor. The residence time in the reactor was about 20 seconds. The reaction product, which had been obtained under adiabatic conditions and was at a temperature of about 160° C., was immediately subjected to phase separation.

The upper, product phase was worked up in known manner (washing with water, washing with soda, 2× washing with water). The yield of isolated product was 170.9 g/h (76.2%). Another 52.0 g/h (23.2%) of product of nitration was obtained by extracting the aqueous acid phase with toluene. The combined products of nitration contained 76% 2,4-dinitrotoluene, 19% 2,6-dinitrotoluene and less than 4.5% o-dinitrotoluenes. The amount of mononitrotoluenes and of trinitrotoluene was in each case less than 1000 ppm (by weight).

EXAMPLE 2

140.3 g/h (1.52 mol/h) of toluene and 3552.5 g/h of nitrating acid having the composition 76.9:5.8:17.3 (parts by weight of $H_2SO_4:HNO_3: H_2O$), corresponding to a molar ratio of nitric acid to toluene of 2.15:1, were continuously pumped into a reactor in which no backmixing could occur from two dosing pumps at 120° C. (temperature of starting materials). The reactor used was a reaction tube of high grade steel 20 m in length and 0.99 mm in internal diameter. The components were mixed immediately before their entry into the reactor. The residence time in the reactor was about 20 seconds. The reaction product obtained under adiabatic conditions, which was at a temperature of about 165° C., was immediately subjected to phase separation.

The upper, product phase was worked up in known manner (washing with water, washing with soda, 2× washing with water). The yield of isolated product was 140.3 g/h (50.6%). Another 134.5 g/h (48.5%) of product of nitration was obtained by extraction of the aqueous acid phase with toluene. The combined products of nitration contained 74.8% 2,4-dinitrotoluene, 18.7% 2,6-dinitrotoluene and less than 5.6% o-dinitrotoluenes. The amount of mononitrotoluenes and of trinitrotoluene present was in each case less than 1000 ppm (weight).

EXAMPLE 3

72.6 g/h (0.788 mol/h) of toluene and 3681.3 g/h of nitrating acid having the composition 78.5:2.9:18.6 parts by weight $H_2SO_4:HNO_3:H_2O$ (corresponding to a molar ratio of nitric acid to toluene of 2.15:1) were continuously pumped into a reactor in which no backmixing could occur from two separate dosing pumps at 140° C. (temperature of the starting materials). The reactor used was a reaction tube of high grade steel 20 m in length and 0.99 mm in internal diameter. The components were mixed immediately before their entry into the reactor. The residence time in the reactor was about 20 seconds. The reaction product obtained under adiabatic conditions, which was at a temperature of 152° C., was immediately subjected to phase separation.

The upper, product phase was worked up in known manner (washing with water, washing with soda, 2× washing with water). The yield of isolated product was 142.4 g/h (99.2%). The amount of mononitrotoluenes and of trinitrotoluene present was in each case less than 1000 ppm (weight).

The waste acids obtained were concentrated and used again after replenishment with fresh nitric acid.

Although the invention has been described in detail in the foregoing for the purpose of illustration, it is to be understood that such detail is solely for that purpose and that variations can be made therein by those skilled in the art without departing from the spirit and scope of the invention, except as it may be limited by the claims.

What is claimed is:

1. A single stage, continuous process for the production of isomeric mixtures of dinitrotoluene comprising
   a) reacting
      (1) toluene with
      (2) a nitrating acid composed of
         (i) from about 80 to about 100% by weight of an inorganic component made up of
            A) from about 60 to about 90% by weight of sulfuric acid,
            B) from about 1 to about 20% by weight of nitric acid, and
            C) at least 5% by weight of water, and
         (ii) from about 0 to about 20% by weight of an organic component containing
            A) from about 70 to about 100% by weight of dinitrotoluene isomers, and
            B) from about 0 to about 30% by weight of by-products under adiabatic conditions and in amounts such that the molar ratio of nitric acid to toluene is maintained at a level of at least 2:1,
   b) continuously removing reaction mixture from the reactor at a temperature of at least 120° C.,
   c) separating the reaction mixture removed in b) into an upper product phase and a lower acid phase,
   d) working up the product phase separated in c) to recover dinitrotoluene,
   e) removing at least 10% of water present in the acid phase separated in c) by flash evaporation,
   f) adding from about 50 to about 100% by weight of nitric acid to the acid phase from e) and
   g) returning the acid phase of f) to a).

2. The process of claim 1 in which the starting materials are at a temperature below 100° C. before being subjected to step a) and the nitrating acid includes from about 5 to about 20% by weight of nitric acid.

3. The process of claim 1 in which the starting materials are at a temperature ≧100° C. before being subjected to step a) and the nitrating acid includes from about 1 to about 15% by weight of nitric acid.

4. The process of claim 1 in which the reaction mixture leaving the reactor in step b) is at a temperature above 120° C., which temperature is at least 10° C. higher than the temperature of the starting materials before they have been subjected to step a).

5. The process of claim 1 in which the product phase is worked up by crystallization in step d).

* * * * *